United States Patent [19]
Bedford et al.

[11] Patent Number: 4,696,819
[45] Date of Patent: Sep. 29, 1987

[54] ANOREXIC MATERIAL EXTRACTED FROM COCA LEAVES AND METHOD OF PREPARING

[75] Inventors: John A. Bedford; Hala N. Elsohly; Marvin C. Wilson, all of Oxford, Miss.; Carlton E. Turner, Alexandria, Va.

[73] Assignee: University of Mississippi, Oxford, Miss.

[21] Appl. No.: 373,695

[22] Filed: Apr. 30, 1982

[51] Int. Cl.$^4$ ............................................. A61K 35/78
[52] U.S. Cl. .................................................. 424/195.1
[58] Field of Search ........................................ 424/195

[56] References Cited

PUBLICATIONS

Morton, Major Medicinal Plants (1977), published by Charles C. Thomas, Springfield, Ill., pp. 177–183.
Furia et al. (Ed.), *Fenaroli's Handbook of Flavor Ingredients* (Cleveland, Ohio, The Chemical Rubber Co., 1971), pp. 15, 91.

*Primary Examiner*—Johnnie R. Brown
*Assistant Examiner*—John W. Rollins, Jr.
*Attorney, Agent, or Firm*—William D. Stokes

[57] ABSTRACT

A naturally occurring anorexic composition of matter that does not alter locomotor function comprising the water soluble constituents of the coca leaf (*Erythroxylon coca*). Anorexic compositions consisting of the foregoing described product prepared from coca leaves in admixture with a non-toxic, pharmaceutically acceptable carrier. A method of suppressing appetite levels in animals comprising administering a therapeutically effective concentration of the inventive product in a pharmaceutically suitable carrier intravenously, orally, intraperitioneally and intramuscularly. The method of preparing an anorexically active product from coca leaves.

8 Claims, No Drawings

ANOREXIC MATERIAL EXTRACTED FROM COCA LEAVES AND METHOD OF PREPARING

The present invention is related to anorexic or appetite suppressant agents and more specifically to the anorexigenic activity of water soluble, cocaine free extracts of the coca leaf (Erythroxylon coca).

It has long been known that certain sympathomimetic drugs, also known as anorexic or adrenergic drugs, for example amphetamines, curb the appetite by stimulating certain centers in the sympathetic nervous system. Unfortunately, substantially all of the known appetite suppressive drugs produce nervous stimulation or locomotor activity so severe that the use thereof is rarely warranted. Moreover, the use of such drugs must be carefully monitored by a physician.

In accordance with the present invention there has been discovered a naturally occurring appetite suppressant material which is non-toxic and has no stimulating effect on the central nervous system to the end that the disadvantages of the known anorexic drugs are overcome and, a method of preparing a drug. The therapeutic agent of the invention comprises the non-cocaine containing water soluble extract derived from the extraction of Erythroxylon coca.

To prepare the anorexic product of the invention, coca leaves are ground to a powder and treated to a first extraction to separate the water soluble compounds and materials from the water insoluble organic constituents containing cocaine present in the leaves. It will be appreciated in the art that this initial extraction step to separate the water soluble compound from the other material present may be carried out in numerous ways, for example, percolation with ethanol, percolation with water, decoction with water, and extraction with an organic solvent followed by extracting the marc by percolation with water. The water extract, which is substantially devoid of cocain, is made basic and further treated by partitioning, or extracting with water and a water immiscible organic solvent that will dissolve water insoluble organic constituents. Suitable organic solvents are ether chloroform, ethyl acetate, or other organic solvents of equivalent polarity. The water extract is evaporated to produce the product, a brownish solid residue, which exhibits remarkable appetite suppressive properties without causing locomotor activity. The product has not been identified either as to physical or chemical structure.

In the preferred embodiment of the invention the aqueous solution is further partitioned for concentration with butanol followed by evaporation to produce the product. The inventive product may be mixed with any non-toxic pharmaceutically diluent carrier and may be effectively administered systemically by any of the usual routes of administration. Among the pharmaceutically acceptable carriers for oral administration are starch, dextrose, sucrose, lactose, gelatin, agar stearic acid and accacia. It will also be appreciated that the product of the invention may be administered intraperitoneally, intravenously and intramuscularly in suitable pharmaceutical carriers.

The following examples exemplify the relative simplicity of preparing the product of the invention and the preparation of the appetite suppressant compositions of the invention.

EXAMPLE I

The Erythroxylon coca used in all of examples set forth herein was collected from the Tingo Maria area of Peru and voucher specimens were deposited in the Herbarium, Research Institute of Pharmaceutical Sciences, School of Pharmacy, University of Mississippi.

2 kg of powdered coca leaves were extracted with 95% ethanol. The ethanolic extract was filtered, then partitioned between water and chloroform. The aqueous layer was concentrated and made alkaline with ammonium hydroxide to a pH 9 and extracted with ether. The aqueous phase from the ether extraction, completely free of cocaine, was subsequently partitioned with butanol. The aqueous fraction was freeze dried to yield 98 g of a brownish amorphous residue, the product of the invention which was labeled Product Sample A and the butanol fraction was evaporated to produce 43 g of the product, a brownish amorphous solid which was labeled Product Sample B for testing.

EXAMPLE II 200 g of produced coca leaves were extracted by percolation with water (1.2 L$\times$3) followed by filtration. The aqueous extract was concentrated to 600 ml in vacuo at 40° and the pH raised to 9 by the addition of ammonium hydroxide followed by extraction with chloroform. The aqueous extract tested free of cocaine was then partitioned with butanol (600 ml$\times$2) The fractions were then treated as in Example I producing 35.7 g of product from the aqueous layer and labeled Product Sample C and 10.2 g product from the butanol layer labeled Product Sample D.

EXAMPLE III 170 g of powdered coca leaves were extracted by decoction with water (1.2 L) for one hour followed by filtration. The aqueous solution was concentrated and made alkaline (pH 9) with ammonium hydroxide followed by extraction with ethyl acetate (200 ml$\times$10). A sample of the cocaine free aqueous layer was removed for testing and the remainder partitioned with butanol and treated as in the preceding examples to produce 25.4 g product (Product Sample E) and 6.8 g product (Product Sample F).

EXAMPLE IV 200 g of produced coca leaves were extracted or defatted by chloroform (1.2 L$\times$2). The marc was then extracted by percolation with water. The aqueous extract was concentrated to 600 ml, made alkaline (pH 9) with ammonium hydroxide followed by extraction with chloroform. The cocaine free aqueous layer was then partitioned as in the proceeding Examples to produce 20.8 g of the product labeled as Product Sample G from aqueous layer and 7.8 g of the product labeled as Product Sample H from the butanol layer.

The product of the invention prepared in the preceding examples was tested for its ability to reduce food consumption in rats. Following an eight to ten day acclimation period during which the test animals had one hour daily access to ground rat chow, groups of ten rats were intraperitoneally injected with sterile distilled water and immediately given access to ground chow for one hour. The amount of chow consumed by each animal was carefully determined. The following day the same group of 10 rats were injected with one of the water solutions of the product prepared in accordance with the method of the Examples. The animals were then given a one hour access to chow and the amount of chow consumed was determined. The results of the tests are set forth in Table I and the results discussed hereinafter. The inventive product was also tested for its ability to alter locomotor activity which testing is discussed in deatil hereinafter.

The test animals used were Male Wistar rats weighing between 200–300 grams at the start of the testing program. Water was freely avilable to the animals in the feeding experiments and available to the animals in the locomotor activity experiments except when the subjects were in the activity measuring device, referred to hereinafter as the "actometer". All test animals were housed individually in galvanized steel suspension cages. Ambient temperature was maintained at $21 \pm 1°$ C. The light/dark cycle was 12 hours light, 12 hours dark. Animals in the activity studies had free access to food up to 18 hours prior to being placed in the actometer. The feeding regimen of the appetite suppressant studies is described in more detail hereafter.

The actometric testing was carried out in donut-shaped photo cell actometers. The design comprises a circular runway with four photocell beams located at substantially 90° intervals around the runway. In the design of this equipment two adjacent beams must be sequentially interrupted for an activity count to be recorded. In this manner a true measure of ambulation is determinable. The experiments were located in a dark temperature controlled room.

The product prepared in accordance with the Examples labeled Product Sample A, B, C, D, E, F, G and H were prepared for injection using sterile water. Injection volume was maintained constant at 2.0 ml/kg. As shown in TABLE I, Product Samples A and B were prepared in a range of dosage units from 60 mg/kg to 960 mg/kg while the product samples C, D, E, F, G and H were prepared in only one dosage unit 480 mg/kg.

At the outset of the experiments all animals were subjected to a four day acclimation period during which the animals had 48 hours access to food in biscuit form followed by 48 hours free access to ground food. The subjects were randomly assigned to experimental groups (n=10). Following the four day acclimation period the animals for the anorexic tests were given 1 hour/day access to ground chow for 10 consecutive days. The amount of food consumed was measured after each days access period. On the day following the 10 day period all subjects in the anorexic testing groups were weighed and dosed with distilled water, the dosage vehicle and immediately given access to the ground chow for one hour. On the following day, the same procedure was followed except that the appropriate dosage unit of product was administered prior to access to chow. Statistical comparisons between vehicle data and product sample data were accomplished via the Wilcoxon Matched-Pairs Signed-Ranks nonparametric test.

The results of the anorexic test utilizing the product of the invention are set out in Table I. It will be seen in the Tables that all of the dosage units of the product of the invention produced a significant reduction in food consumption at one or more of the doses tested.

TABLE I

The Effects of Several Doses of Two Water Soluble, Cocaine Free Extracts on Food Consumption

| Extract | Dose (mg/kg) | Mean ± Standard Error Grams Food Consumed | | % Reduction in Food Consumption |
|---------|--------------|-------------------------------------------|--------|--------|
|         |              | Vehicle | Extract | |
| A | 120 | 10.53 ± .9 | 9.55 ± .39 | 9% |
| A | 240 | 9.20 ± .56 | 8.98 ± .43 | 2% |
| A | 480 | 9.23 ± .58 | 7.50 ± .48 | 19% |
| A | 960 | 9.20 ± .65 | 7.78 ± .53* | 15% |
| B | 60 | 8.39 ± .47 | 7.22 ± .34* | 14% |
| B | 120 | 11.03 ± .45 | 6.17 ± .70* | 44% |
| B | 240 | 9.49 ± .82 | 4.90 ± .94* | 48% |
| B | 480 | 9.03 ± .4 | 2.16 ± .63* | 76% |
| B | 960 | 8.64 ± .53 | 1.43 ± .09* | 84% |
| C | 480 | 9.8 ± .84 | 3.7 ± .65* | 62% |
| D | 480 | 10.3 ± .96 | 6.4 ± .36* | 38% |
| E | 480 | 9.8 ± .64 | 2.6 ± .38* | 73% |
| F | 480 | 10.8 ± .65 | 5.9 ± .83* | 45% |
| G | 480 | 9.4 ± 1.22 | 4.8 ± .62* | 49% |
| H | 480 | 10.0 ± 1.0 | 6.3 ± .57* | 37% |

*$P \leq .05$. Wilcoxon Matched-Pair Signed-Ranks Test.

The product does not alter locomotor activity. After the acclimation period, the animals assigned for actometric testing were randomly assigned to individual groups of 10. On the afternoon prior to testing (18 hours prior to testing time) food was removed in order to control for deprivation state since this may influence locomotor activity. Dosage units of 60, 120, 240 and 480 mg/kg of the product samples in distilled water was administered intraperitoneally immediately prior to testing. The vehicle control for all product samples was distilled water. A session consisted of a 60 minute determination of activity, recorded at 15 minute intervals. No charge in locomotor activity was observed in any of the animals tested.

Having shown and described the invention and several embodiments thereof it will be readily apparent that various modifications and substitutions may be made without departing from the spirit and scope thereof.

We claim:

1. The method of preparing an anorexigenic cocaine free compound or mixture of compounds from coca leaves (Erythroxylon coca) comprising the first step of grinding the leaves to fine powder; second, extracting the water soluble constituents from the powder; third, treating the water soluble constituents with a base to make alkaline; fourth, extracting the water soluble constituents with water and a water immiscible organic solvent that will dissolve water insoluble organic constituents; fifth, separating the water extract from the orgainc solvent extract; and sixth, evaporating the water extract to obtain a solid residue.

2. The method of claim 1 wherein the water extract of said fifth step is partitioned with butanol followed by evaporation of the butanol fraction to obtain a solid residue.

3. The method of claim 1 wherein the solid residue is obtained by freeze drying.

4. The method of claim 1 wherein the organic solvent is selected from the group consisting of chloroform, ether, ethylacetate and solvents of equivalent polarity.

5. The compound or components prepared from coca leaves in accordance with claim 1.

6. An anorexigenic composition consisting essentially of the compound or components of claim 5 in admixture with a non-toxic pharmaceutically acceptable carrier.

7. An anorexigenic composition consisting essentially of the solid residue of claim 2 in admixture with a non-toxic pharmaceutically acceptable carrier.

8. A method of suppressing appetite in mammals which comprise administering to mammals the composition of claim 7, said composition containing said solid residue in a therapeutically effective concentration.

* * * * *